United States Patent [19]

Joens et al.

[11] Patent Number: 5,110,589
[45] Date of Patent: May 5, 1992

[54] SWINE DYSENTERY SUBUNIT VACCINE AND METHOD

[75] Inventors: Lynn A. Joens; James D. Cramer; Mary E. Mapother, all of Tuscon, Ariz.

[73] Assignee: Arizona Technology Development Corporation, Tucson, Ariz.

[21] Appl. No.: 244,725

[22] Filed: Sep. 14, 1988

[51] Int. Cl.$^5$ .................. A61K 39/02; A61K 35/14
[52] U.S. Cl. ........................ 424/92; 42/88; 530/350; 530/395
[58] Field of Search ............ 424/92, 88; 530/350, 530/395

[56] References Cited

U.S. PATENT DOCUMENTS

| | | | |
|---|---|---|---|
| 4,152,413 | 5/1979 | Goodnow | 424/92 |
| 4,152,415 | 5/1979 | Harris et al. | 424/92 |
| 4,758,517 | 7/1988 | Parizek | 435/253 |

FOREIGN PATENT DOCUMENTS

| | | |
|---|---|---|
| 282965 | 9/1988 | European Pat. Off. |
| 350715 | 1/1990 | European Pat. Off. |
| 88/04555 | 6/1988 | World Int. Prop. O. |
| 88/04778 | 6/1988 | World Int. Prop. O. |

OTHER PUBLICATIONS

Kinyon et al., "Growth of *Treponema hyodysenteriae* in liquid medium" The Veterinary Record, vol. 95, pp. 219–220, 1974.

Joens et al., *Infection and Immunity*, vol. 54, No. 3, pp. 893–896, Dec. 1986.

Hubbard et al., *Conference of Research Workers in Animal Diseases*, Reference #300, Nov. 1986.

Miller et al., *Conference of Research Workers in Animal Diseases*, Reference #D-151 Nov. 1986.

Primary Examiner—Margaret Moskowitz
Assistant Examiner—Abdel A. Mohamed
Attorney, Agent, or Firm—David G. Rosenbaum

[57] ABSTRACT

The present invention relates to a method for the preparation of a swine dysentary subunit vaccine. The swine dysentery subunit vaccine is composed of antigenic material harvested from the surface of an anaerobic spriochete, *Treponema hyodysenteriae*. The bacterial cells, previously grown in large volume (5-7 liters) in a bench-top fermentor, are harvested by centrifugation and washed vigorously in phosphate buffered saline. The bacterial cells are then removed by a second centrifugation and the supernatant retained. The supernatant contains a salt extract consisting of the antigenic material used in the vaccine. Once harvested, the salt extract is concentrated 100X. The salt extract has been shown to be immunogenic in pigs. Five to six week old pigs are hyperimmunized intramuscularly (IM) with the salt extract. Pigs vaccinated with the salt extract are protected against infection with *Treponema hyodysenteriae*.

12 Claims, 2 Drawing Sheets

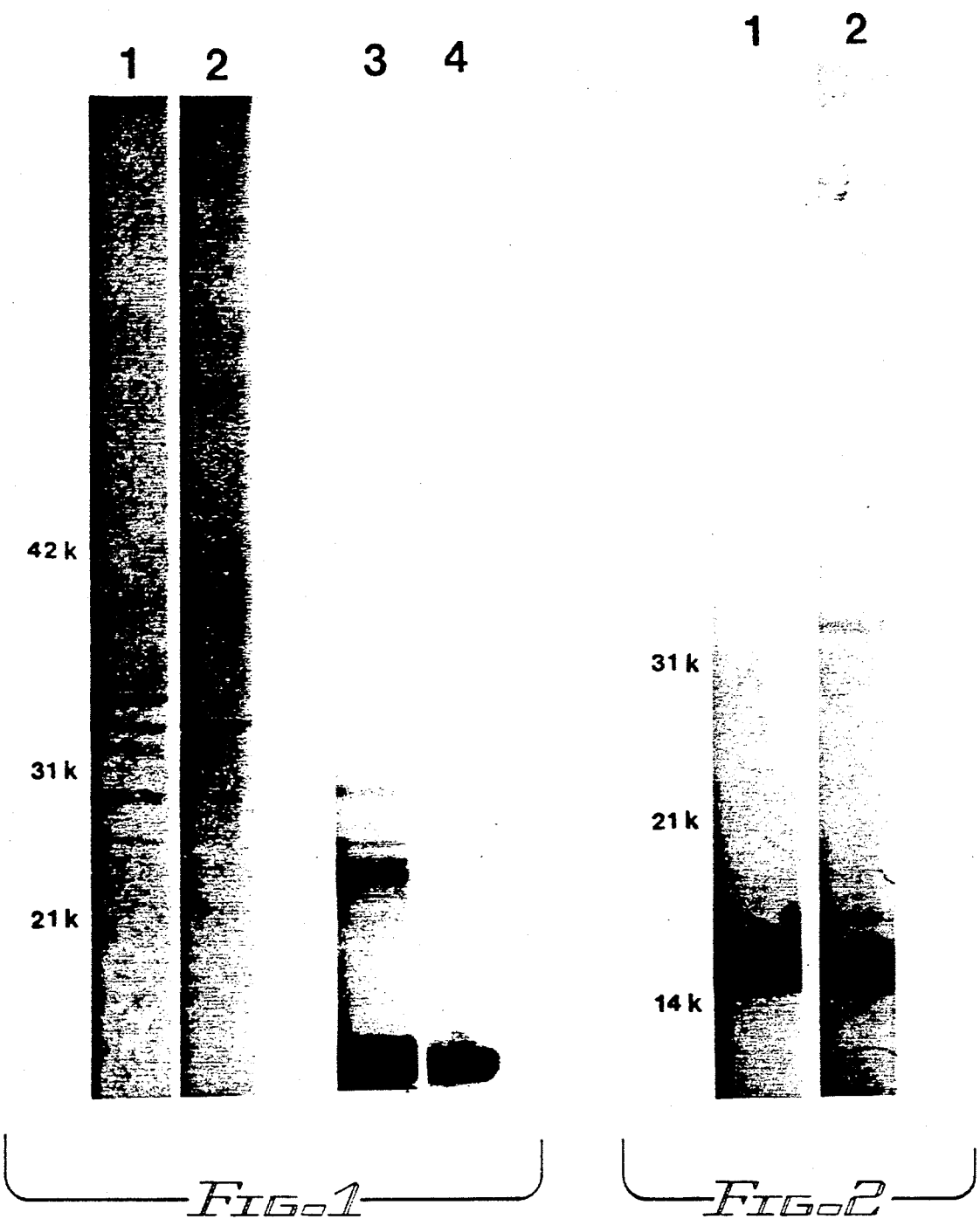

SWINE DYSENTERY SUBUNIT VACCINE AND METHOD

BACKGROUND OF THE INVENTION

The present invention relates generally to a method for preparing a swine dysentery vaccine. This invention relates more particularly to a swine dysentery subunit vaccine that has been shown to be protective against infection with *Treponema hyodysenteriae* and the pathogenesis associated with swine dysentery.

There is a pressing need for a swine dysentery vaccine that is immunogenic in swine, protects against *Treponema hyodysenteriae* infection, and is not harmful to those who consume the pork. At present, there is no vaccine available that would offer all of these features combined. The present invention provides immunogenic protection against swine dysentery resulting from *T. hyodysenteriae*.

The use of killed whole cells of *T. hyodysenteriae* is well known in the art. Examples of vaccines and methods of use of various whole cell veccine preparations are found in U.S. Pat. Nos. 4,469,672, 4,203,968, 4,152,414 and 4,152,415 all to Delbert L. Harris; U.S. Pat. No. 4,152,413 issued May 1, 1979 to Robert A. Goodnow; PCT Appiication No. PCT/GB85/00087, International Publication No. WO 85/03875, Applicant: National Research Development Corporation and European Patent Application No. 86105860.0 filed Apr. 28, 1986, Applicant: Mobay Corporation.

In contrast to the whole cell preparations of the prior art, the present invention provides a sub-unit preparation from the outer envelope portion of *Treponema hyodysenteriae* which is demonstrated to have antigenic activity. Characterization of the sub-unit preparation indicates that the sub-unit portion consists of a protein enriched carbohydrate mixture of outer-membrane proteins (OMP) and lipopolysaccharide (LPS) of *T. hyodysenteriae*.

SUMMARY OF THE INVENTION

To resolve the difficulties encountered with swine dysentery, it is an object of the present invention to provide a new and improved swine dysentery vaccine.

It is a further object of the present invention to provide a process for the preparation of a swine dysentery subunit vaccine that protects vaccinuted pigs against infection with *Treponema hyodysenteriae*, and is not harmful to humans that consume the pork.

It is a further object to employ antigenic material harvested from the outer membrane envelope of the bacteria *Treponema hyodysenteriae*. The antigenic material is obtained in a two step process. First, the bacterial cells are harvested by means of a first centrifugation. The bacterial cells are resuspended with phosphate buffered saline (1800 ml/4 l harvest) and a second centrifugation separates the outer envelope portion of the whole cells from the cytoplasmic material. It is only the outer membrane portion which is used to yield the antigenic material. This antigenic material thus obtained will be referred to as "salt extract." Once harvested, the salt extract is concentrated 100X.

The foregoing and other objects, features, and advantages of the invention will be apparent from the following, more particular, description of the compositions and the preferred embodiment of the invention, as illustrated in the accompanying tables, and figures.

BRIEF DESCRIPTION OF THE FIGURES

FIG. 1 (Lanes 1 & 2) is a Sodium Dodecyl SulfatePolyacrylamide Gel Electrophoresis (SDS-PAGE) pattern of sarcosylextracted OMP's from a whole cell lysate (Lane 1) and from a salt extract (Lane 2) of *Treponema hyodysenteriae* strain B234 following staining with Coomassie blue. Molecular size markers in kilodaltons are shown on the left. FIG. 1 (Lanes 3 & 4) is a Western blot of outer membrane antigens from the whole cell lysate (lane 3) and salt extract (lane 4) of *T. hyodysenteriae* strain B204. The transblottad outer membrane antigens were stained with convalescent swine sera (first antibody', and peroxidase labelled biotin-avidin anti-swine IgG (second antibody) The bands were visualized by adding the substrate 4-chloro-1-naphthol. Molecular size markers in kilodaltons are shown on the left.

FIG. 2 is a Western blot of LPS extracted antigens (Lane 1) and sarcosyl-extracted antigens (Lane 2) from the salt extract of *T. hyodysenteriae* strain B204. The transblotted outer-membrane antigens were stained with convalescent swine sera (first antibody) and peroxidase labelled biotin-avidin anti-swine IgG (second antibody). The bands were visualized by adding the substrate 4-chloro-1-napthol. Molecular size marker in kilodaltons are shown on the left.

DETAILED DESCRIPTION OF THE PREFERRED EMBODIMENT

Figure 3:
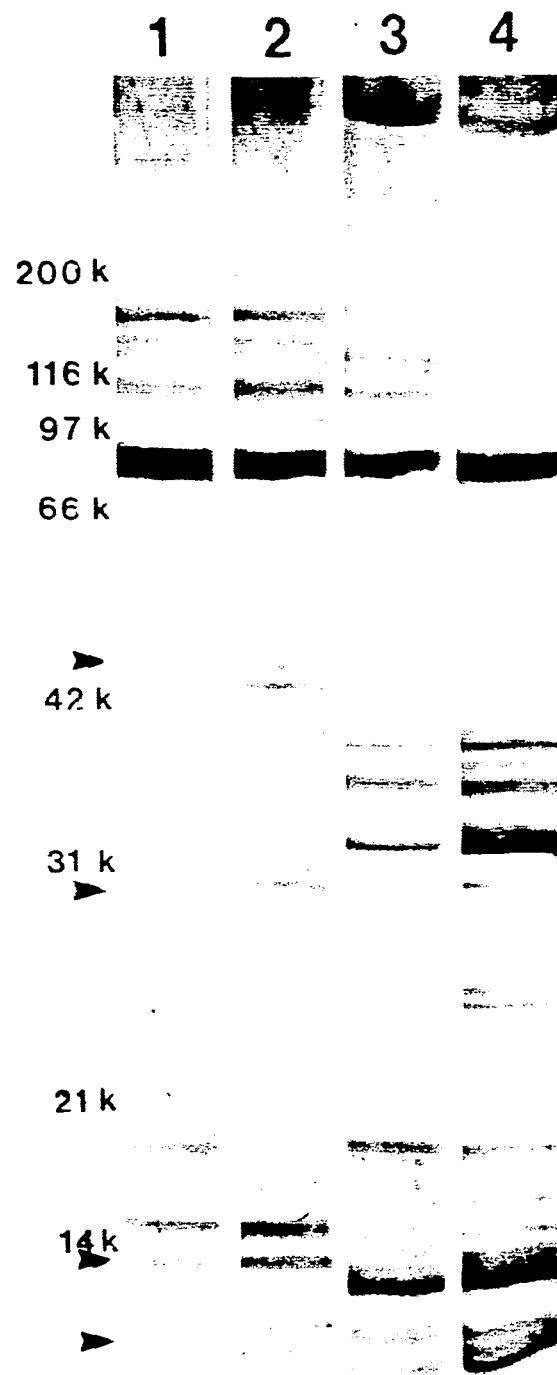
FIG. 3 is a SDS-PAGE pattern of salt extracts visualized by silver staining. Lanes 1 and 2 are salt extracts from serotype 1 and 2 *T. hyodysenteriae* which were protective in CF-1 mice, whereas, lanes 3 and 4 are salt extracts from both serotypes which were not protective in mice.

The instant invention presents a swine dysentery subunit vaccine composed of antigenic material harvested from the surface of the bacteria *Treponema hyodysenteriae*. The antigenic material contains both proteins and lipopolysaccharide (LPS) from the outer membrane portion of the cell wall of the spirochete. Antigens from the outer-membrane are known to be involved in the generation of the immune response by the host to various gram-negative organisms, including *Leqionella pneumophila*, *Haemophilus influenzae* and *Haemophilus pleuropneumoniae*. Heretofore, however, it has been not been shown th:t outer-membrane antigens of *Treponema hyodysenteriae* are antigenic and involved in the immune response of the host to swine dysentery.

The antigenic activity of the envelope portion of *Treponema hyodysenteriae* was determined by further fractioning the salt extract into outer-membrane proteins (OMP) and lipopolysaccharide (LPS) and reacting the portions against convalescent antisera. In general, the bacteria were grown by fermentation under anaerobic conditions, harvested by centrifugation, washed in phosphate buffered saline and harvested by a second centrifugation. The envelope fraction ("sole extract") was removed from the cell wall during the second centrifugation stap, and pelleted by ultracentrifugation. The pellet was divided into two portions; the first portion was treated with sodium N-lauroyl sarcosinate (Sarcosyl) and the OMP's harvested by ultracentrifugation. The second portion was extracted with phenowater to obtain the LPS portion of the envelope. SDS-PAGE was performed on both portions of the envelope and on sarcosyl extracted whole cells of *Treponema hyodysenteriae* using a discontinuous SDS-slab gel electrophoresis technique. Electrophoretic transfer of the antigens from gels to paper was performed by the western blotting method. Antigens were identified by reacting convalescent swine sera to the transblotted proteins and carbohydrates as shown in FIGS. 1 and 2.

According to the preferred embodiment, as illustrated by the following example, there is shown a process for separating the salt extract from the whole cell of *T. hyodysenteriae*. It will be understood, by those skilled in the art, that the following example is not intended to limit the scope of the invention and that alternative methods of preparing and isolating the antigenic salt extract are contemplated and within the intended scope of the present invention.

EXAMPLE

1. Preparation of the bacterial cells of *Treponema hyodysenteriae*:

The preparation of the bacterial cells comprises the utilization of an anaerobic spirochete, *Treponema hyodysenteriae*.

The bacteria was grown in a bench-top fermentor containing trypticase soy broth supplemented with about 2.5-5% fetal bovine serum and 2-5% porcine fecal extract under an atmosphere of 10% $H_2$, 10% $CO_2$, and 80% $N_2$. Following 42 hours incubation at 37° C., the bacterial cells were harvested by centrifugation (6500 rpm, 30 min) and washed vigorously in phosphate buffered saline.

2. Preparation of the antigenic material used in the subunit vaccine ("salt extract")

To obtain the antigenic material used in the subunit vaccine, the bacterial cells, obtained by the process explained in step one, were then removed by a second centrifugation (6500 rpm, 30 min) and the supernatant retained. The supernatant contained the antigenic material used in the vaccine. Once harvested, the salt extract was concentrated 100X using a YM10 membrane in an Amicon ultrafiltration unit, filtered through a sterile 0.45 μm membrane, aliquoted, assayed and stored frozen in liquid nitrogen.

Five separate assays were used in characterizing the salt extract. They include:

(1) The antigenic reaction against various polyclonal and monoclonal antibody in the enzyme-linked immunosorbent assay (ELISA),
(2) The ability of the washing antigen to block the attachment of *Treponema hyodysenteriae* to Henle intestinal epithelial (HIE) cells in vitro,
(3) The swine dysentery subunit SDS-PAGE profile after staining with silver stain,
(4) The protein profile after separation with QAE ionexchange chromatography, and
(5) Immunogenicity in CF1 mice and pigs.

TABLE I

|  | Antibody used in ELISA | | |
|---|---|---|---|
|  | Convalescent B204 swine sera #38 (1:50 dil.) | Rabbit B204 hyperimmune sera (1:100 dil.) | Unexposed swine sera PIC (1:50 dil.) |
| O.D. Response | >1.0 | <0.4 | <0.4 |

The antibody used in the ELISA are as follows: convalescent B204 swine sera #38 (1:50 dilution), rabbit B204 hyperimmune sera (1:100 dilution), and unexposed swine sera PIC (1:50 dilution). The reaction of the washing antigen to the various antibody in the ELISA showed a high optical density (O. D.) response (>1.0) to convalescent B204 swine sera #38, and a low response (<0.4) to the other sera.

The in vitro attachment inhibition assay involved seeding tissue culture plates with HIE 407 cells and allowing them to attach to the plastic surface. A 0.3 ml volume of the salt extract in 1.7 ml of Minimal Essential Media (MEM) was added to the epithelial cells, and incubated. Following incubation, the epithelial cells were rinsed, and 0.7 ml of a log-phase culture of *T. hyodysenteriae* in 1.3 ml of MEM was added to the epithelial cells and incubated. The epithelial cells were once again rinsed, and stained with Wright's stain for microscopic examination. Results show that the salt extract significantly inhibits the ability of *T. hyodysenteriae* to attach to the epithelial cell as compared to the control epithelial cell which was not pretreated with the salt extract.

The salt extract has been shown to be immunogenic in the CF1 mouse model. Twenty one day old CF1 mice were hyperimmunized intraperitoneally (IP) with 0.15 ml amounts of salt extract incorporated into ary injectable adjuvant, such as the Ribi adjuvant, approved by the United States Food and Drug Administration. Alternatively, for experimental purposes, Freunds or MVP adjuvant may be used. The mice were injected with the vaccine on days 1 and 14, then intragastrically challenged 10 and 11 days after the second vaccination with $10^7$–$10^8$ a cells of *T. hyodysenteriae*. Following an additional 10 day incubation period, the mice were necropsied and examined for lesions in the cecum. Mice vaccinated with the salt extract were protected against the development of lesions as compared to the control, non-vaccinated mice which developed lesions typical of swine dysentery.

The salt extract also exhibited immunogenic activity in swine. Six week old pigs were hyperimmunized intramuscularly (IM) with 2.5 ml of the salt extract incorporated into Freund's complete or Ribi adjuvant on days 1 and 14. Pigs were then challenged on day 28 with $10^7$–$10^8$ a cells of *T. hyodysenteriae*. Following a 30 day incubation period during which pigs were observed for clinical signs of dysentery, the animals are necropsied and examined for lesions in the colon and cecum. Pigs vaccinated with the salt extract were protected against infection with *T. hyodysenteriae* as compared to the non-vaccinated, control pigs which developed typical lesions of swine dysentery. Furthermore, vaccinated pigs showed no clinical signs of the disease but may or may not shed the bacteria in their feces.

The clinical response of the pigs inoculated with salt extract versus the control pigs is set forth below in Table 1.

| Treatment | Cases[1] | Dysentery Onset[2] | Dysentery Duration[3] | Dysentery Deaths[4] |
|---|---|---|---|---|
| Salt Extract[5] | 0/12 | 0 | 0 | 0/12 |
| Control[6] | 10/12 | 13 | 14 | 6/12 |

[1]Number of Pigs with dysentery/total number of pigs.
[2]Day blood was observed in feces following challenge.
[3]Number of days blood was observed in feces.
[4]Number of pigs that died of dysentery/total number of pigs.
[5]Salt Extract mixed with Freund's Complete Adjuvant (1:1) (v/v).
[6]Sterile phosphate buffered saline (pH 7.2) mixed with Freund's Complete Adjuvant (1:1) (v/v).

Treatment of the salt extract with either Proteinase K or sodium-M-periodate resulted in loss of immunogenicity as determined by the CF1 mouse model system, suggesting that both protein and carbohydrate may be active portions of the antigen. Carbohydrate analysis using the method of Dubois has shown that salt extracts which contain high amount of carbohydrate show the greatest degree of immunogenicity in CF1 mice.

Salt extracts separated by SDS-PAGE and silver stained have been used to differentiate extracts which are protective from extracts which are nonprotective in the CF-1 mouse models. As illustrated in FIG. 3, profiles of protective extracts contain a triplet of bands between 47-43 kDa, and three sets of doublet bands at 35-33, 14-12, and 10-8 kDa which are absent in gels containing nonprotective extracts. The bands which are in the range of 47-43, 14-12, and 10-8 kDa are labile in extracts which are stored at 4° C. This demonstrates the importance of protein as a viable component of the subunit vaccine.

Comparison studias between individral surface components of the spirochete using the Western blot assay has demonstrated that lipopolysaccharides (LPS) and sarcosyl insoluble outer-membrane proteins (OMP) are included in the salt extracts from the organism. Antisera from immune pigs vaccinated with salt extract recognize OMP and LPS antigens of *T. hyodysenteriae*. Also, antisera derived against the lipopolysaccharide molecule of strains B204 and B234 *T. hyodysenteriae* recognize the antigens which are part of the salt extract. Sarcosyl insoluble OMP enriched fractions from *T. hyodysenteriae* were prepared from whole cell lysates and salt extracts, separated by SDS-PAGE and examined for differences. As illustrated in FIG. 1 (Lanes 1 & 2), six to seven protein bands were resolved for both extracts of *T. hyodysenteriae* ranging from 49 to 28 kDa. The OMP profiles were similar between the whole cell lysate and the salt extract of *T. hyodysenteriae*. The outermembrane antigens detected in lanes 3 and 4 are identified by convalescent swine sera in both sarcosyl extracted whole-cell lysates and sarcosyl extracted salt extracts of *T. hyodysenteriae*. Similar bands were identified by sera in both extracts. As shown in FIG. 2, a diffuse staining band of the salt extract at 14 kDa is visualized in Western blotting after phenol-water extraction of the salt extract components (Lane 1) or after sarcosyl extraction of the salt extract components (Lane 2). This diffuse staining antigen exhibited similar staining pattern characteristics to that of *T. hyodysenteriae* lipopolysaccharide in Western blots and was present only in the pathogenic species. The presence of carbohydrate in sarcosyl extractions appears to be species related. It seems probable, therefore, that the carbohydrate portion of the OMP molecule is the active antigenic component.

Analysis by HPLC QAE ion-exchange chromatography of the salt extract has revealed 9 distinct protein peaks within a 0–1.0 M NaCl ramp gradient separation. Nine of the forty fractions collected within these peaks were reactive in the ELISA against convalescent swine sera #38. One of these fractions which demonstrated a high response to convalescent sera in the ELISA (Fraction #12) was immunogenic in CF1 mice (n=5). Western blot analysis of fraction 12 demonstrated the presence of 12 antigenic bands when reacted to homologous hyperimmune mouse sera ranging from 92-16 kDa. Two of the antigens at 92 and 16 kDa were extracted from nitrocellulose by affinity precipitation incorporated into Freund's complete adjuvant, and injected into rabbits for the production of antisera. Antisera derived against both of the antigens were shown to be reactive against salt extracts in the ELISA and bacteriocidal to *T. hyodysenteriae* in the presence of swine complement.

The results of the foregoing clearly point to the carbohydrate fraction as exhibiting antigenic activity alone or in combination with the protein fraction. Thus, according to the preferred embodiment of the present invention, there has been isolated a protein/carbohydrate antigenic fraction of *T. hyodysenteriae*, which exhibits immunogenic activity against swine dysentery.

Principally, the method of the present invention contemplates two steps. First, a method for the preparation of bacterial cells of *T. hyodysenteriae*. Second, a method for the preparation of the antigenic material used in the subunit vaccine.

While the invention has been particularly shown and described with reference to a certain protein/carbohydrate subunit antigen of *T. hyodysenteriae* and to the method for preparing a swine dysentery subunit vaccine thereof, it will be understood by those skilled in the art that the foregoing and other changes in composition and details, including alternative methods of obtaining and isolating the protein/carbohydrate antigenic fraction may be made therein without departing from the spirit and scope of the invention.

We claim:

1. A process for preparing a swine dysentery subunit vaccine comprising the steps of: growing *Treponema hyodysenteriae* by fermentation in tryptcase soy broth supplemented with bovine serum and porcine facel extract under an anaerobic atmosphere; harvesting the *Treponema hyodysenteriae* bacterial cells; separating an outer envelope portion of said *Treponema hyodysenteriae* bacterial cells from a cytoplasmic portion of said *Treponema hyodysenteriae* bacterial cells; and mixing said outer envelope portion with an injectable adjuvant.

2. The process according to claim 1, wherein said step of harvesting said bacteria *T. hyodysenteriae* further comprises the step of harvesting following about 24–42 hours incubation at about 37°–42° C. by means of centrifugation.

3. The process according to claim 1, wherein said separating step further comprises washing said harvested bacterial cells of *T. hyodysenteriae* with a phosphate buffered saline solution, centrifuging said resulting solution thereby separating said outer envelope portion from said cytoplasmic portion.

4. The process according to claim 1, further comprising the step of concentrating said outer envelope portion.

5. The process according to claim 4, wherein said step of mixing further comprises mixing said concentrated outer envelope portion with Ribi adjuvant.

6. The process according to claim 1, wherein said bovine serum is present in about 2.5-5% and said porcine fecal extract is present in about 2-5%.

7. A process for preparing a swine dysentery subunit vaccine comprising the steps of: growing *Treponema hyodysenteriae;* harvesting the *Treponema hyodysenteriae* bacterial cells; separating an outer envelope portion of said bacterial cells of from cytoplasmic portion of said bacterial cells; isolating an antigenic fraction of said outer envelope portion, wherein said antigenic fraction is characterized by a broad staining band under Western blot assay at 16 KDa; and mixing said outer envelope portion with an injectable adjuvant.

8. The process according to claim 4, wherein said step of concentrating said outer envelope portion further comprises the step of isolating an antigenic fraction of said outer envelope portion, wherein said antigenic fraction is characterized by a broad staining band under Western blot assay eluting at about 16 kDa.

9. The process according to claim 7, wherein said step of growing said bacteria *T. hyodysenteriae* comprises growing said bacteria through fermentation in a trypticase soy broth supplemented with bovine serum and porcine fecal extract under an anaerobic atmosphere.

10. The process according to claim 7, wherein said step of harvesting said bacteria *T. hyodysenteriae* further comprises the step of harvesting following about 24-42 hours incubation at about 37°-42° C. by means of centrifugation.

11. The process according to claim 7, wherein said separating step further comprises washing said harvested bacterial cells of *T. hyodysenteriae* with a phosphate buffered saline solution, centrifuging said resulting solution thereby separating said outer envelope portion from said cytoplasmic portion.

12. The process according to claim 7, further comprising the step of concentrating said outer envelope portion.

* * * * *

UNITED STATES PATENT AND TRADEMARK OFFICE
CERTIFICATE OF CORRECTION

PATENT NO. : 5,110,589
DATED : May 5, 1992
INVENTOR(S) : Lynn A. Joens  et al

It is certified that error appears in the above-indentified patent and that said Letters Patent is hereby corrected as shown below:

In Claim 1, line 3, change "tryptcase" to --trypticase--.

In Claim 1, line 4, change "facel" to --fecal--.

In Claim 7, line 9, change "KDa" to --kDa--.

Signed and Sealed this

Fourteenth Day of September, 1993

*Attest:*

BRUCE LEHMAN

*Attesting Officer*  *Commissioner of Patents and Trademarks*